United States Patent
Okada et al.

(10) Patent No.: US 8,688,328 B2
(45) Date of Patent: Apr. 1, 2014

(54) APPARATUS AND METHOD FOR MOVEMENT CONTROL OF A VEHICLE

(75) Inventors: Tadayoshi Okada, Wako (JP); Toshiaki Arai, Wako (JP)

(73) Assignee: Honda Motor Co., Ltd., Tokyo (JP)

(*) Notice: Subject to any disclaimer, the term of this patent is extended or adjusted under 35 U.S.C. 154(b) by 124 days.

(21) Appl. No.: 13/257,223

(22) PCT Filed: May 14, 2010

(86) PCT No.: PCT/JP2010/003275
§ 371 (c)(1),
(2), (4) Date: Nov. 4, 2011

(87) PCT Pub. No.: WO2010/134304
PCT Pub. Date: Nov. 25, 2010

(65) Prior Publication Data
US 2012/0046844 A1    Feb. 23, 2012

(30) Foreign Application Priority Data
May 20, 2009    (JP) ................................ 2009-122453

(51) Int. Cl.
*B60W 30/00* (2006.01)
*B60W 10/04* (2006.01)
*B60W 10/18* (2012.01)
*B60T 7/12* (2006.01)

(52) U.S. Cl.
USPC ............................................. 701/48; 701/70

(58) Field of Classification Search
None
See application file for complete search history.

(56) References Cited

U.S. PATENT DOCUMENTS

| 2005/0143893 | A1 | 6/2005 | Takamatsu et al. |
| 2006/0111823 | A1* | 5/2006 | Tamai ............................. 701/38 |
| 2007/0050120 | A1 | 3/2007 | Tabata et al. |
| 2007/0096557 | A1* | 5/2007 | Tamai et al. .................. 303/191 |
| 2008/0154472 | A1* | 6/2008 | Okuda et al. ..................... 701/93 |
| 2010/0262349 | A1* | 10/2010 | Braeuer ......................... 701/70 |
| 2011/0065548 | A1* | 3/2011 | Yu et al. ........................ 477/203 |

FOREIGN PATENT DOCUMENTS

| DE | 10303415 A1 * | 8/2004 |
| DE | 102007046307 A1 * | 4/2009 |
| JP | 81-278454 A | 12/1986 |
| JP | 10-166897 B2 | 6/1998 |

(Continued)

OTHER PUBLICATIONS

Japanese Office Action dated Aug. 20, 2013, 2 pages.

(Continued)

*Primary Examiner* — Michael J Zanelli
(74) *Attorney, Agent, or Firm* — Arent Fox LLP

(57) ABSTRACT

When a start-up operation by a driver is detected while a vehicle is maintained at a stopped state, a target driving force for suppressing the movement of the vehicle on the road to be driven is calculated, based on the grade obtained regarding the road to be driven on. After the vehicle is driven by the target driving force, the braking force is released so as to terminate the maintaining of the stopped state of the vehicle. Preferably, the state of being driven by the target driving force is maintained until the releasing of the braking force is completed. When the releasing of the braking force is completed, the driving force is increased to start-up the vehicle. With such a start-up control, vehicles are prevented from moving temporarily in a direction opposite from the traveling direction, and a smooth star-up can be achieved.

10 Claims, 8 Drawing Sheets

(56) References Cited

FOREIGN PATENT DOCUMENTS

| | | |
|---|---|---|
| JP | 2002-162225 A | 6/2002 |
| JP | 2002-262594 A | 9/2002 |
| JP | 2004-108589 A | 4/2004 |
| JP | 2005-186788 A | 7/2005 |
| JP | 2006-056398 A | 3/2006 |
| JP | 2006-069420 A | 3/2006 |
| JP | 2006-151369 A | 6/2006 |
| JP | 2006-199154 A | 8/2006 |
| JP | 3853447 B2 | 9/2006 |
| JP | 2007-055536 A | 3/2007 |
| JP | 2007-283882 A | 11/2007 |
| WO | WO2009/043740 A1 * | 4/2009 |

OTHER PUBLICATIONS

Chinese Office Action, Chinese Application No. 201080020048.9 dated Nov. 19, 2013.

* cited by examiner

APPARATUS AND METHOD FOR MOVEMENT CONTROL OF A VEHICLE

CROSS REFERENCED TO RELATED APPLICATION

This application is a National Stage entry of International Application No. PCT/JP2010/003275, filed May 14, 2010, which claims priority to Japanese Patent Application No. 2009-122453 filed May 20, 2009, the disclosure of the prior application is incorporated in its entirety by reference.

TECHNICAL FIELD

The present invention relates to an apparatus and method for movement control of a vehicle.

BACKGROUND OF THE INVENTION

Japanese patent 3853447 (Patent Literature 1) describes an apparatus for controlling creep movement of a vehicle. According to the apparatus, when a means for detecting operation of the brake detects no operation of the brake, creep movement control for the vehicle at a predetermined target speed is performed. In accordance with the inclination of the road, intake air amount is feedback controlled with an intake air amount control unit.

PRIOR ART LITERATURE

Patent Literature

Patent Literature 1: Japanese Patent 3853447

SUMMARY OF THE INVENTION

Problem to be Resolved by the Invention

When the brake is in a released state, at the instant that the brake is released, inclination of the road may give acceleration to the vehicle in a reverse direction from the direction the vehicle is moving. Such reverse acceleration may disturb driver's feeling and may hamper secure driving.

Accordingly, it is an object of the present invention to provide a movement control capable of avoiding lowering of driver's feeling when a vehicle stops and starts on an inclined road.

Means for Resolving the Problem

According to an aspect of the present invention, while the vehicle is held in stop position with braking control, when starting operation by the driver is detected, starting control is activated. In the starting control, based on acquired data on inclination of the road, a target driving force (balancing power) that suppresses movement of the vehicle by inclination is calculated. After the vehicle is driven with the target driving force, the braking force that has held the vehicle in stop position is released. Responsive to release of the braking force, the driving force is increased to start the vehicle.

According to the present invention, when the vehicle is driven with the target driving force that suppresses movement of the vehicle on the road, the stop state of the vehicle is held by the driving force that counteracts the inclination. That is, it is not that the vehicle is held in the stop position by the braking force. Accordingly, as the braking force (power) is released while the target driving force (power) is applied to the vehicle, the vehicle would not move in a reverse direction. Thus, the vehicle may be started smoothly without disturbing the driver's feeling.

In one embodiment of the present invention, the condition that the vehicle is driven by the target driving force is maintained until release of the braking force finishes. The vehicle is kept driven by the target driving force until the braking force is completely released. Accordingly, the driver is released from the feeling of dragging when the braking force is released and is released from the sense of abruptness when the braking force is completely released.

According to one embodiment of the present invention, the target driving force is calculated responsive to the magnitude of the inclination so that the vehicle would not move as the braking force is released. As the target driving force is calculated based on the inclination to provide sufficient power to maintain the stop state of the vehicle for any inclination of the road.

According to one embodiment of the present invention, the starting control of the vehicle is activated when the vehicle is to drive upward an inclined road. According to the invention, the vehicle is prevented from moving in a direction reverse to an advancing direction, thus enabling a smooth start of the vehicle.

According to one embodiment of the present invention, irrespective of the driver's operation on the acceleration pedal, the vehicle is driven by the target driving force until release of the braking force finishes. Thus, irrespective of the operation on the acceleration pedal, the vehicle may be start smoothly, thus accomplishing a secure starting control.

The other characteristics and advantages of the present invention will be evident from the following description.

DETAILED DESCRIPTION OF PREFERRED EMBODIMENTS

Now, with reference to the drawings, preferred embodiments of the present invention will be described.

Figure 1:
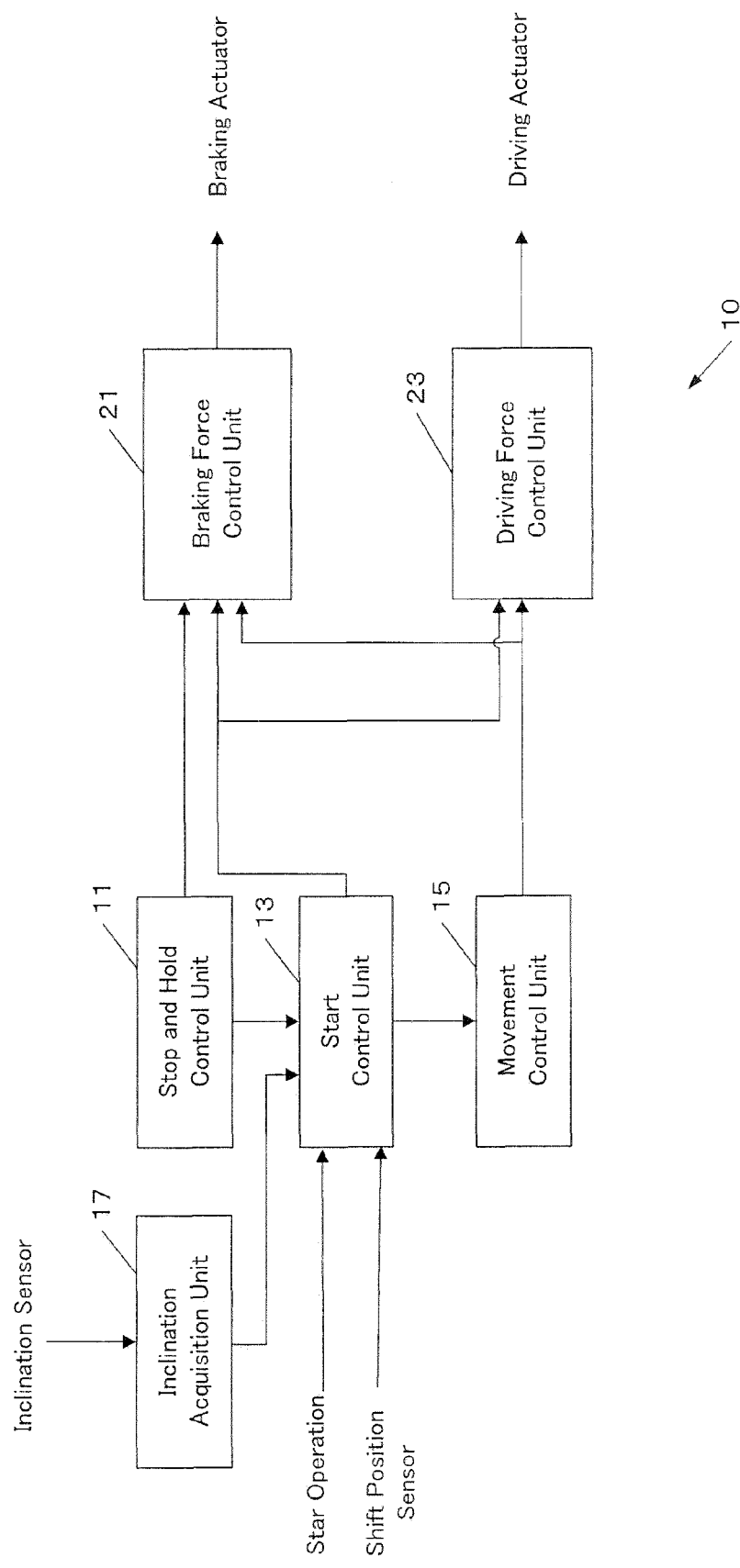
FIG. 1 is a block diagram of one embodiment of the movement control apparatus of the present invention.

FIG. 1 is a block diagram of one embodiment of the movement control apparatus 10 of the present invention that is provided onboard a vehicle for controlling movement of the vehicle. Movement control apparatus 10 is accomplished with an electronic control unit (ECU) that is essentially a computer having a central processing unit (CPU) and a memory. The functional blocks illustrated in FIG. 1 are provided by the CPU.

Movement control apparatus 10 comprises stop and hold control unit 11, start control unit 13, movement control unit 15, braking force control unit 21 and driving force control unit 23.

Stop and hold control unit 11 provides commands to braking force control unit 21 to hold the stop state of the vehicle. Braking force control unit 21 is connected to a brake actuator (not shown) that controls mechanical elements for applying braking force to the vehicle. Braking force control unit 21, responsive to commands from stop and hold control unit 11, controls the brake actuator to hold the vehicle in stop state. The mechanical elements that apply braking force to the vehicle may be conventional elements, and may be a liquid pressure brake device or an electrically powered parking brake.

While stop state of the vehicle is held by stop and hold control unit 11, responsive to detection of start operation by the driver, start control unit 13 sends a command to braking force control unit 21 to release stop and hold state initiated by the command from stop and hold control unit 11, and sends a command to driving force control unit 23 to provide a driving force for starting the vehicle. Braking force control unit 21, responsive to a command from start control unit 13, controls brake actuator to release braking force applied to hold stop-state of the vehicle.

Driving force control unit 23 is connected to a driving actuator (not shown) that controls mechanical elements for applying driving force to the vehicle. Driving force control unit 23, responsive to a command from start control unit 13, The mechanical elements for applying driving force to the vehicle may be conventional elements, and for example may include a throttle valve that controls the amount of intake air to the engine, and intake air valves. The amount of intake air may be controlled by adjusting the degree of the throttle valve, or by adjusting lift amount of the intake air valve. For a vehicle such as a hybrid car that utilizes a motor in addition to an engine to drive the vehicle, the mechanical elements may include the motor. With the control of the motor, the driving force may be controlled.

Movement control unit 15 controls movement of the vehicle after start control by start control unit 13 has finished. Via braking force control unit 21 and, driving force control unit 23, driving at a constant speed, acceleration and deceleration are accomplished.

The start operation by the driver may include operation of a switch for starting the vehicle or an operation of pressing down the accelerator pedal.

For stop and hold control unit 11, start control unit 13 and movement control unit 15 may be accomplished by using a low speed following mode of a automatic following control system that controls the vehicle to automatically follow a preceding car in a relatively low speed region and controls automatic stop and start. With the automatic following control, the preceding car is detected by a radar system, and when the preceding car stops, the system stops the vehicle and holds it in a stop state. The system, responsive to operation of the start switch, releases the stop and hold state and starts the vehicle to follow the preceding car. Such following control system is described in, for example, Japanese Patent Application Publication (JPAP) No. 2006-56398, JPAP 2006-69420, and JPAP 2006-151369.

Referring to FIG. 1 again, movement control apparatus of the present invention further comprises inclination acquisition unit 17, which acquire inclination of the road when the vehicle is running along the road. The inclination may be acquired with any appropriate scheme. In one embodiment, the vehicle includes a sensor for detecting inclination of the road (pitch angle of the vehicle). Inclination acquiring unit 17 acquires inclination of the road from the values detected by the sensor. In another embodiment, the vehicle is provided with a G sensor that detects acceleration degree in the moving direction of the vehicle. Inclination acquiring unit 17 may estimate the inclination of the road based on the values detected by the G. Such estimating scheme is described in, for example, JPAP 2002-162225. In further other embodiments, inclination acquiring unit 17b may determine the inclination of the road based on output torque, braking force and other factors of the vehicle. Such scheme is described in, for example, JPAP 2004-108589, JPAP 2007-283882 and others.

Figure 2:
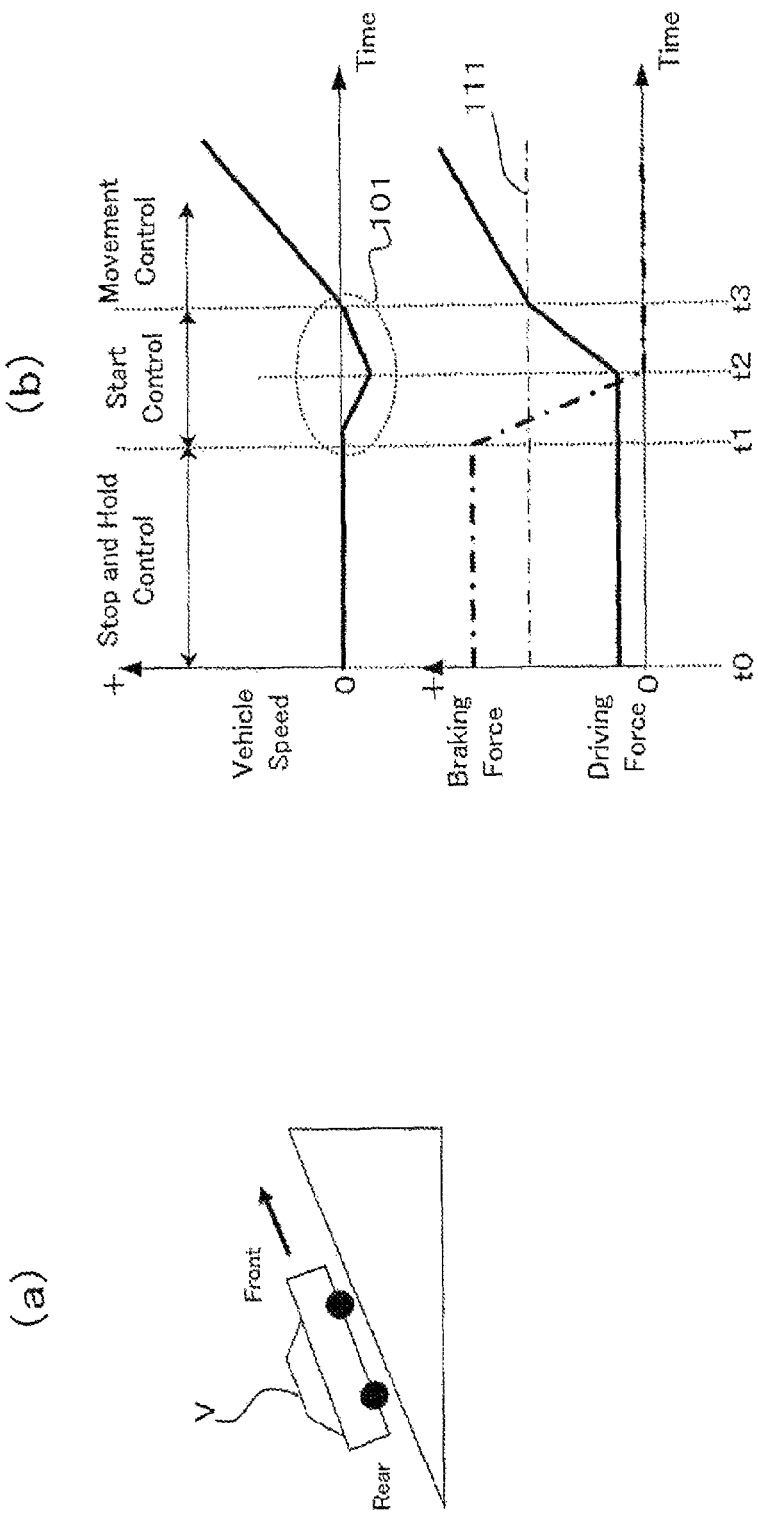
FIG. 2 illustrates a starting control of prior art.
Figure 3:
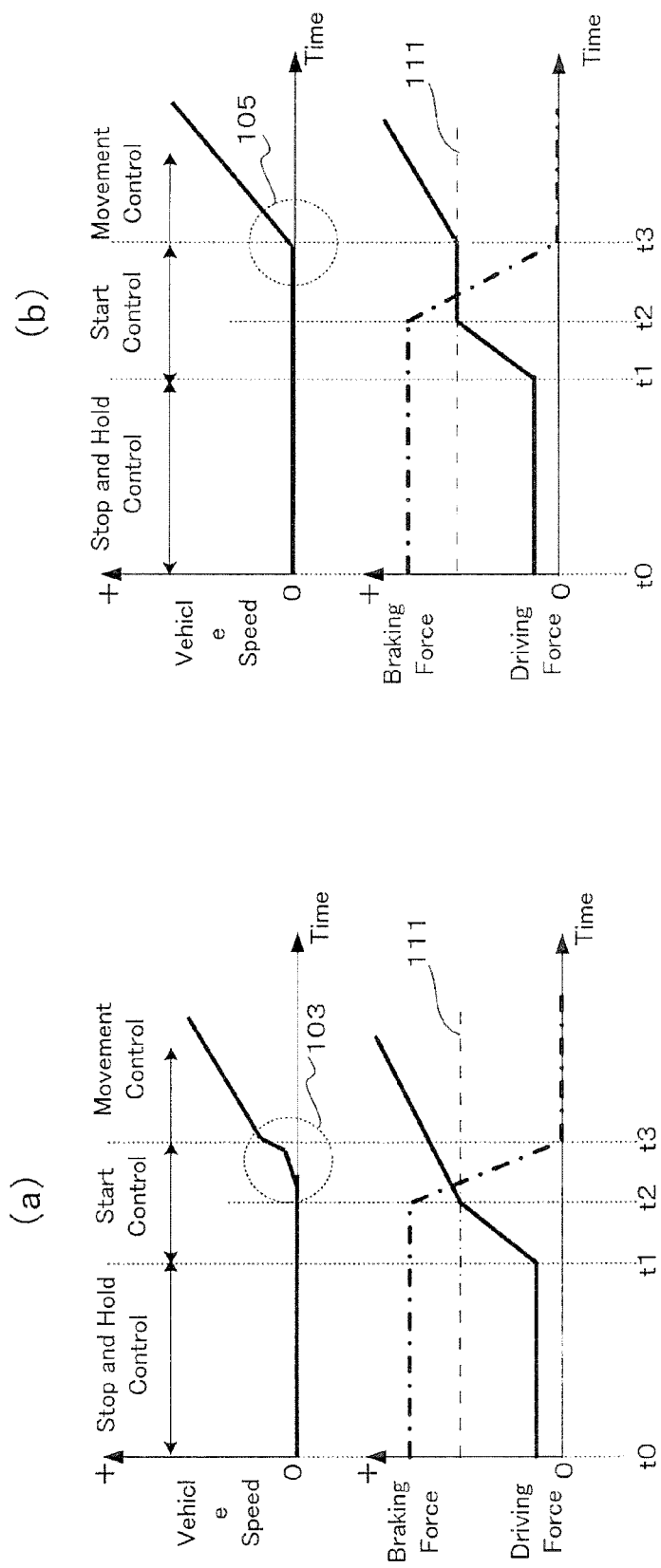
FIG. 3 illustrates a starting control according to one embodiment of the present invention.

Start control unit 13, in addition to the above mentioned start control, utilizes the inclination acquired by inclination acquiring unit 17 to accomplish a smooth start of the vehicle that is held in stop state on an inclined road. Referring to FIGS. 2 and 3, basic principles of the present invention will be described.

FIG. 2(*a*) illustrates a vehicle V stopped on an inclined road. The vehicle is going to start in the direction indicated by an arrow. That is, the vehicle is going to start in the front or forward direction. Let's assume that the inclination is too large for the vehicle to keep in stop state by a predetermined creep power that works on the vehicle.

FIG. 2(*b*) illustrates transition of vehicle speed, braking force (dotted line) and driving force (solid line) in a conventional start control. Vehicle speed has a positive value when the vehicle moves forward and has a negative value when the vehicle moves backward.

In FIG. 2(*b*), stop state of the vehicle is held by braking force during time t0-t1. Driving force is maintained at a predetermined low value (creep power). Dotted line 111 indicates the driving force that is needed to balance the inclination. That is, in order to maintain the vehicle in the stop and hold state on an inclined road, a force needs to be applied to the vehicle that balances the gravity working on the vehicle. Dotted line 111 indicates the magnitude of driving force needed to hold the vehicle in the stop and hold state on this inclined road without braking force.

At time t1, the driver makes a start operation, responsive to which start control begins. According to the start control, when braking force is completely released (to 0) at time t2, driving force starts to increase. When the driving force reaches line 111, which is the driving force needed to balance with the inclination, the vehicle starts to move forward.

With this start control, acceleration generates in a reverse direction to the moving direction temporarily in the region indicated by a circle 101, the vehicle moves backward temporarily. The driver may be given a feeling that the vehicle is slipping down the slope, which would hurt the driver's feeling.

FIG. 3(*a*) illustrates transition of vehicle speed, braking force (dotted line) and driving force (solid line) that takes place when start control in accordance with the present invention is performed in a state similar to FIG. 2(*a*). During time t0-t1, the vehicle is held in stop state by the braking force. At time t1, responsive to the driver performing start operation, start control begins. According to the start control, driving force starts to increase at time t1, and when the driving force reaches line 111 (time t2) that represents an inclination power that is driving force needed to balance with the inclination, braking force starts to be released. The driving force continues to increase until the braking force is completely released (time t2-t3).

With this manner of start control, the braking force is released after the driving force is increased, the problem observed with FIG. 2(*b*), that is, the phenomenon that the vehicle temporarily moved in a reverse direction is prevented. Thus, the driver's feeling would be better than in FIG. 2(b).

However, with this start control, increase of the vehicle speed may fluctuate as indicated in circle 103. That is, at time t2 where the braking force starts to be released, the vehicle speed may start to gradually increase and may abruptly increase when the braking force reaches zero at time t3. While the vehicle speed gradually increases, the driver may feel that the vehicle is dragged, and when the vehicle speed increases abruptly, the driver may feel abruptness.

Thus, in a preferred embodiment of the present invention, start control as illustrated in FIG. 3(b) is performed. In a similar manner as FIG. 3(a), FIG. 3(b) illustrates transitions of vehicle speed, braking force (dotted line), and driving force (solid line). The start control is on the basis of a similar state as in FIG. 2(a). During time t0-t1, the vehicle is held in stop state by the braking force. Responsive to the driver's operation to start the vehicle, start control begins. In the start control, driving force is increased while braking force is maintained (time t1), which is the same as in FIG. 3(a). In this start control, when the driving force reaches line 111 (time t2), the braking force starts to be released. While the braking force is being released, the driving force is maintained to balance with the inclination power. When the braking force is completely released (to become 0) at time t3, the driving force is increased from the value that balances with the inclination power to start the vehicle.

With this start control, increase of the driving force is suppressed so that it does not take place while the braking force is being decreased. Thus, the problem as described with reference to FIG. 3(a) resolves. That is, during time t2-t3, the driving force is maintained to balance with the inclination power and the vehicle maintains the stop and hold state by the driving force without needing the braking force. Accordingly, when the braking force starts to decrease, the vehicle speed stays zero without providing a feeling of being dragged to the driver. When the braking force becomes zero, the driving force starts to increase. Thus, as shown in the region of circle 105, the vehicle speed increases smoothly to accomplish a smooth start.

In FIGS. 3(a) and (b), the stop and hold state during time t0-t1 is accomplished by stop and hold control unit 11 and the start control during time t1-t3 is accomplished by start control unit 13. Movement after start at time t3 is accomplished by movement control unit 15.

Figure 4:
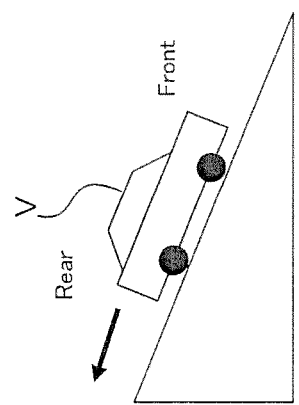
FIG. 4 illustrates a manner of starting a vehicle in a backward direction.

In the example of FIG. 3, the vehicle started to move forward to go up the slope. FIG. 4 illustrates an example where the vehicle moves backward to go up the slope. A similar start control is performed. In this case, the power to balance the inclination power 111 for moving backward may differ from that for moving forward. Accordingly, as illustrated in FIG. 1, start control unit 13 receives detection signal from a shift position sensor and calculates the driving force needed to balance the inclination power according to the shift position, forward (D) or backward (R).

Figure 5:
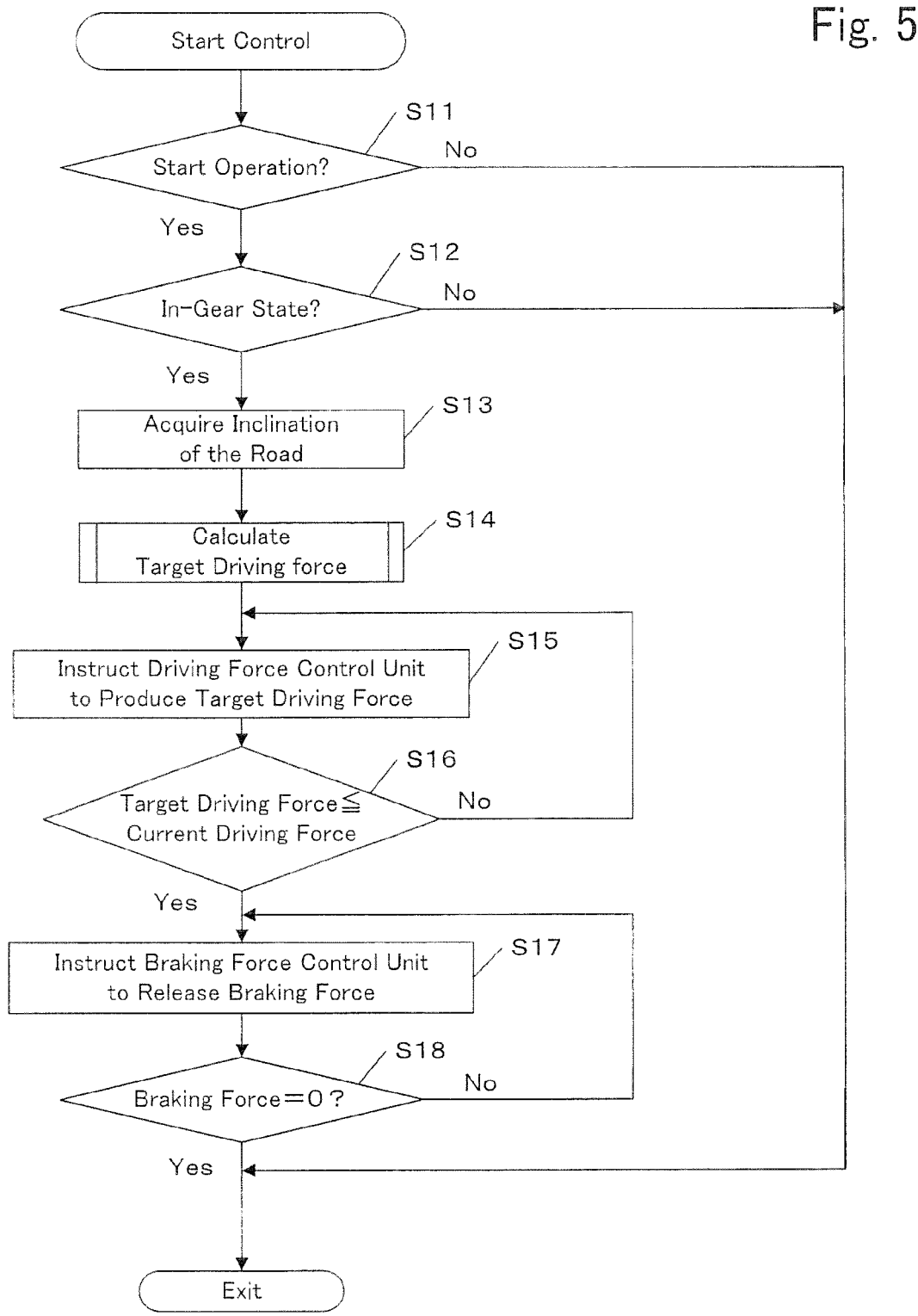
FIG. 5 is a flow chart of a process of start control according to one embodiment of the present invention.

FIG. 5 is a flowchart of a process performed by start control unit 13. The process is on the basis of the start control as illustrated in FIG. 3(b).

In step S11, determination is made if the driver's start operation is detected. As mentioned above, this determination may be made by detecting operation of a predetermined start switch or by detecting pressing down of the accelerator pedal. When the start operation is not detected, the process terminates.

When the start operation is detected, detection signal from shift position sensor is acquired in step S12 and determination is made if the shift position indicated by the detection signal indicates an in-gear state. That is, determination is made whether the gear is in drive forward (D) position or in move backward (R) position. If the shift position indicates drive forward (D) or move backward (R), the process moves to step S13. If the shift position does not indicate an in-gear state, that is, if the shift position is in neutral (N) or in parking (P), the process terminates.

In step S13, the inclination of the road along which the vehicle is running is acquired based on detection signals from, for example, an inclination sensor and other detectors. In step S14, the driving force to counteract the power from the inclination 111 as illustrated in FIG. 3(b) is calculated and output as a target driving force (balancing power). The details of this calculation will be described later.

In step S15, a command is sent to driving force control unit 23 to control the current driving force to match the target driving force (balancing power). In step S16, determination is made if the current driving force reached the target driving force. If negative, the process moves back to step S15 to continue driving force control. If positive, the process moves to step S17 to send a command to braking force control unit 21 to release braking force. Release of braking force should be performed as quickly as possible so that the vehicle may start moving quickly.

In step S18, determination is made if the braking force has become zero. If negative, the process returns to step S17 to continue braking force control. If positive, it means that the start control has completed. After that, movement control unit 15 increases the driving force gradually from the value of the target driving force (balancing power, the value of dotted line 111) as illustrated in FIG. 3(b) to gradually increase the vehicle speed, whereby the vehicle starts moving smoothly.

Next, referring to FIG. 6, calculation of the target driving force (balancing power) in step 14 will be described.

FIG. 6(a) illustrates the relationship between the driving force and acceleration when the vehicle is moving forward (shift position D) along an inclined road. Braking force is assumed to be zero.

In FIG. 6(a), "climbing" indicates that the direction from the rear to the front of the vehicle is upwardly inclined and the inclination is indicated by positive value. "descending" indicates that the direction from the rear to the front of the vehicle is downwardly inclined and the inclination is indicated by negative value. C1 indicates a value of inclination that provides gravity to balance with a predetermined creep power applied to the vehicle.

Figure 6:
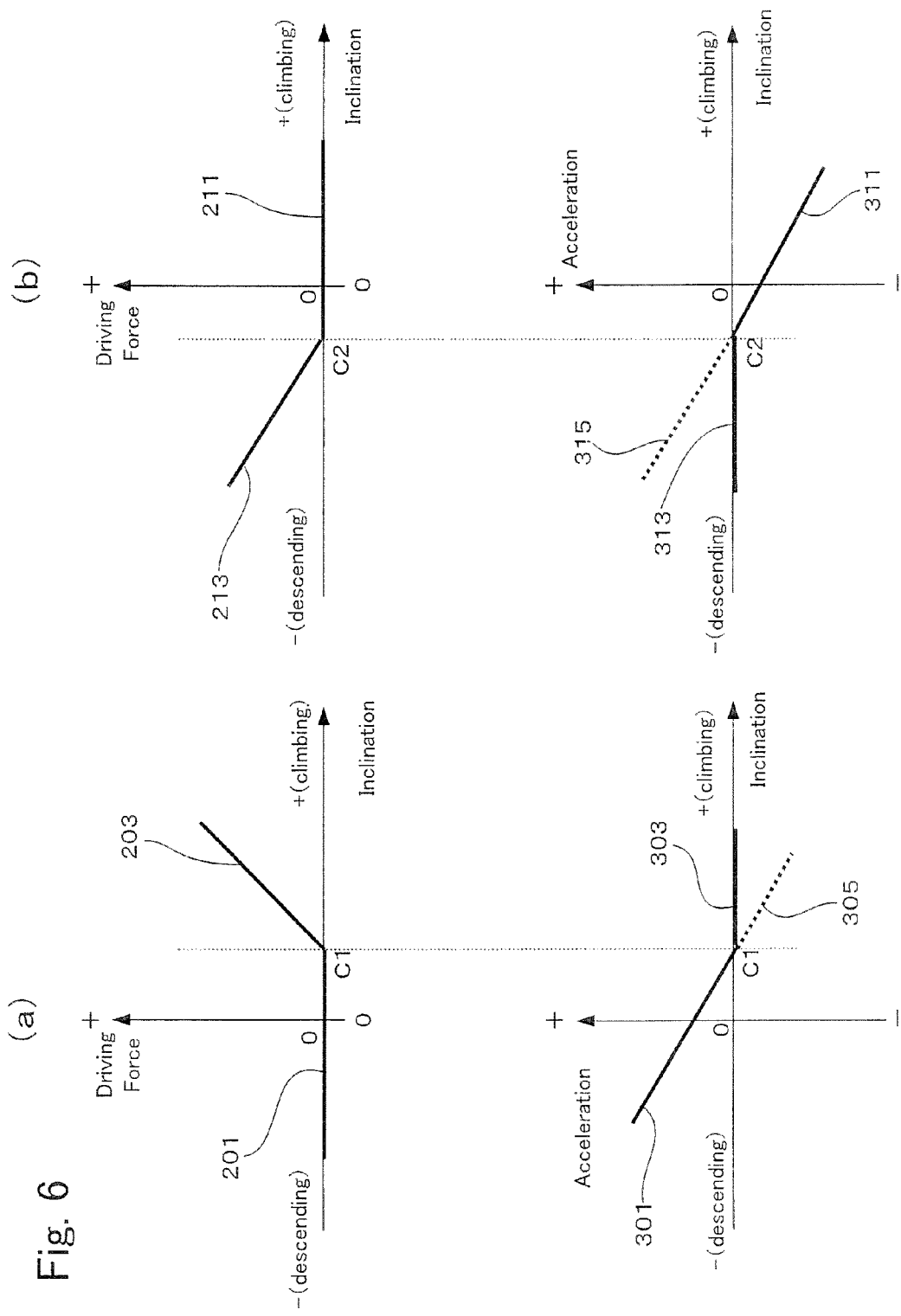
FIG. 6 illustrates the target driving force according to inclination of the road in one embodiment of the present invention.

In FIG. 6 the upper chart indicates driving force applied to the vehicle, and the lower chart indicates corresponding acceleration of the vehicle. Acceleration value is positive in the direction of forward movement of the vehicle, and negative in the direction of backward movement. When the inclination is C1, acceleration of the vehicle is zero and the vehicle is in a stop state.

When the inclination is smaller than C1 as indicated by solid line 201, the driving force is controlled to be zero, responsive to which acceleration increases as the inclination becomes smaller (downward inclination becomes larger).

When the inclination is equal to or larger than C1 as indicated by solid line 203, the driving force is increased as the inclination becomes larger so that acceleration becomes zero. As indicated by solid line 303, acceleration is maintained at zero.

Dotted line 305 indicates acceleration when the inclination is equal to or larger than C1 and when the driving force is brought to zero. In this case, the acceleration has a negative value indicating that the vehicle will move backward. Driving force indicated by solid line 203 in FIG. 6(*a*) such movement to a reverse direction may be suppressed.

When the vehicle is to start moving forward, the target driving force (balancing power) may be set with reference to a driving force map such as the one shown in the upper part of FIG. 6(*a*). This way, when the climbing inclination is equal to or larger than C1, driving force that balances with the inclination is applied to the vehicle so that the vehicle may be held in stop state even if the braking force is zero.

FIG. 6(*b*) illustrates the relation between the driving force and acceleration with respect to inclination of the road when the vehicle is to move backward (with shift position R). In the drawing, "climbing" and "descending" have the same meaning as FIG. 6(*a*).

C2 indicates the value of inclination where a predetermined creep power balances with the inclination, that is, where the power caused by the gravity counteracts or cancels the creep power. The upper part of FIG. 6(*b*) illustrates the driving force applied to the vehicle, while the lower part illustrates acceleration (solid line) caused by such driving force. Acceleration has a negative value for backward direction of the vehicle and has a positive value for forward direction. At inclination C2, acceleration of the vehicle is zero and the vehicle is in stop state.

When the inclination is larger than C2 as indicated, the driving force is controlled to be zero as indicated by solid line 211. Correspondingly, acceleration becomes larger as the inclination becomes larger (climbing inclination becomes larger).

When the inclination is equal to or smaller than C2, the driving force is increased as the value of inclination decreases to make acceleration zero as indicated by dotted line 213. As can be seen in the lower part of the drawing, acceleration is maintained at zero as indicated by solid line 313.

For the inclination equal to or smaller than C2, dotted line 315 indicates the acceleration when the driving force is zero. Here, the acceleration has a positive value indicating that the vehicle will be dragged forward to descend the slope. The driving force indicated by solid line 213 prevents the vehicle from moving in a reverse direction.

When a driver wishes to start moving backward, the target driving force may be set in accordance with the driving force map as shown in the upper part of FIG. 6(*b*). With such a setting, even if the descending inclination is equal to or lower than C2, a driving force to balance with the inclination is applied to the vehicle so that the vehicle is held in stop state if braking force is zero.

Figure 7:
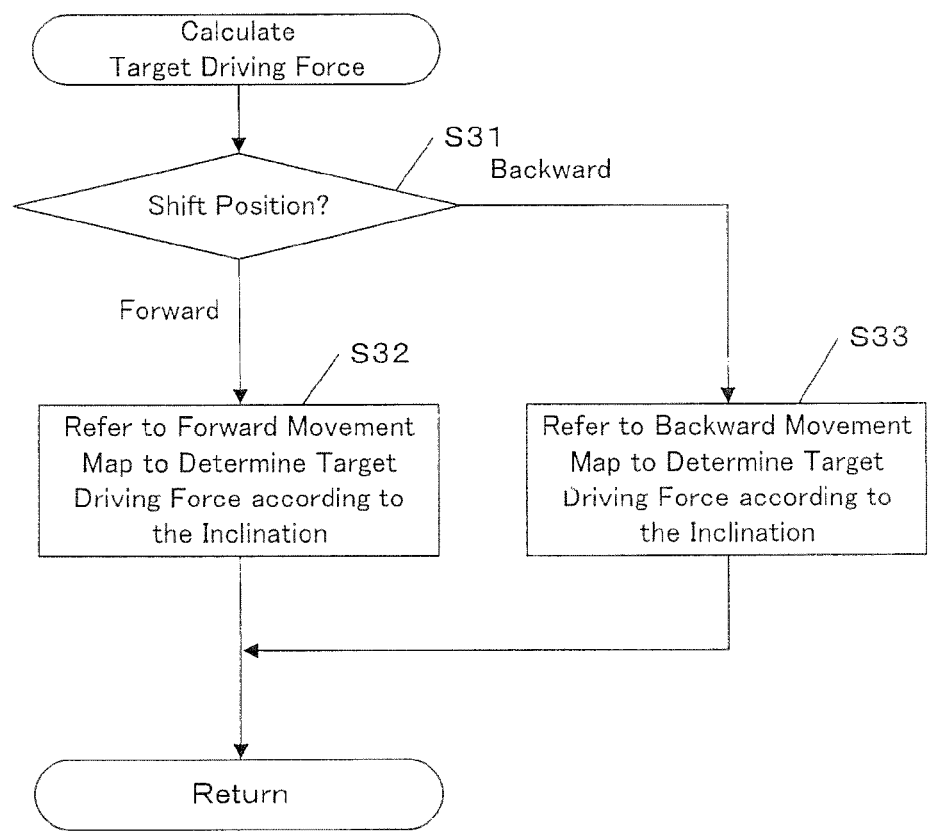
FIG. 7 is a flow chart of a process for calculating the target driving (balancing) power according to one embodiment of the present invention.

FIG. 7 is a flow chart of the process for calculating the target driving force (balancing power) to be performed in step S13 of FIG. 5 in accordance with the scheme described with reference to FIG. 6.

In step S31, determination is made which movement the shift position acquired in step S12 (FIG. 5) indicates, forward movement (shift position D) or backward movement (shift position R). If it indicates forward movement, the process moves to step S32, in which forward movement map as shown in the upper part of FIG. 6(*a*) is referred to according to the inclination of the road acquired in step S12 to determine a target driving force. Such map may be stored in the memory of movement control apparatus 10.

If the shift position indicates backward movement, the process moves to step S33, in which the backward movement map as shown in the upper part of FIG. 6(*b*) is referred to according to the inclination acquired in step S12 to determine target driving force. Such map may also be stored in the memory of movement control apparatus 10.

Thus, when the descending direction of the road is opposite to the direction the vehicle is going to start moving, a target driving force to balance with the magnitude of inclination is calculated. As such target driving force is applied to the vehicle, the driver would not be given a feeling that the vehicle is being dragged when he or she starts the vehicle. The vehicle is held in the stop state by the target driving force until braking force is completely released. Thus, the driver may start the vehicle without sensing incongruity.

Figure 8:
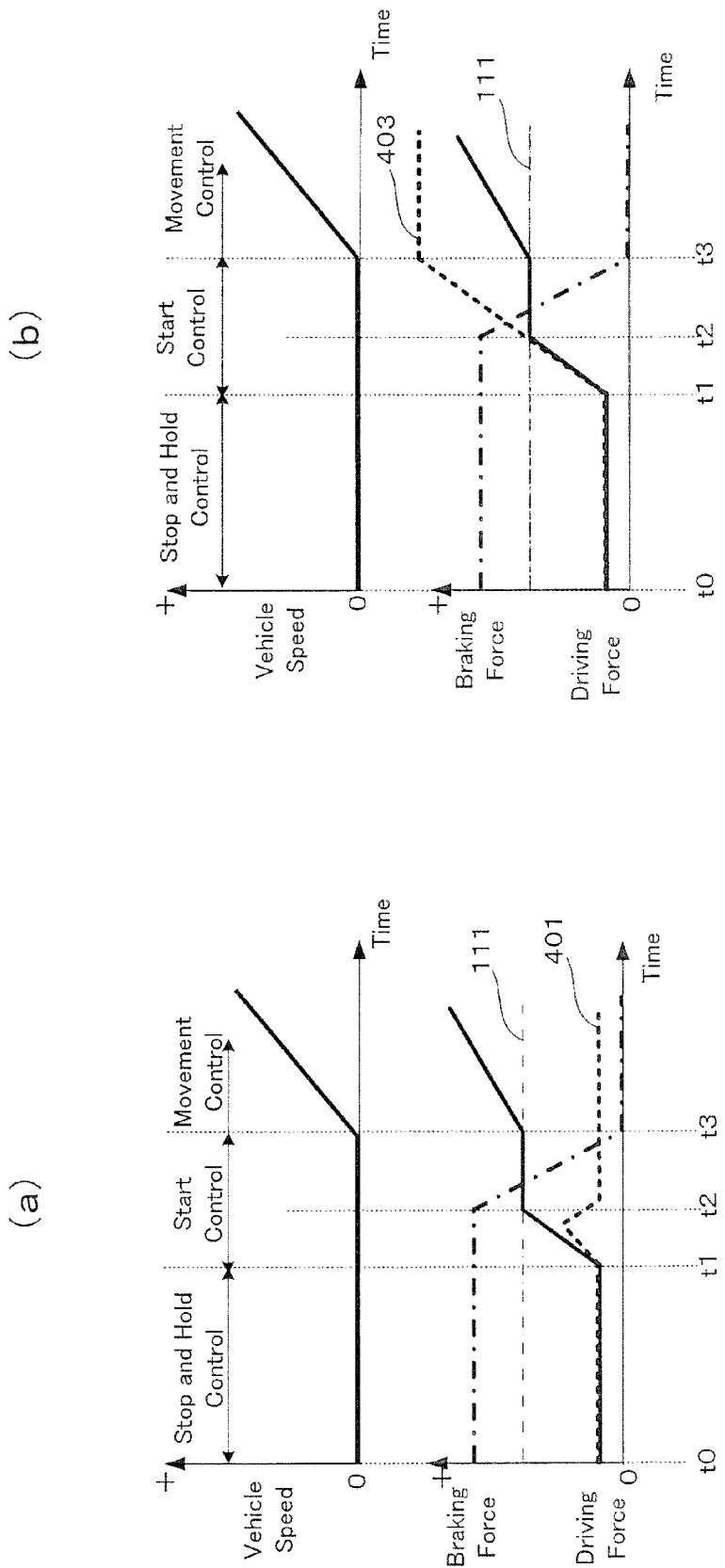
FIG. 8 illustrates starting operation to be performed irrespective of the amount of activation of the acceleration pedal according to one embodiment of the present invention.

Referring to FIG. 8, the relation between the above described starting control of the present invention and accelerator pedal operation by the driver will be described. When movement control apparatus 10 is performing a start control, the driver may press on the accelerator pedal. Normally, the driving force of the vehicle is controlled responsive to the degree of operation on the accelerator pedal (operation angle). However, in the start control of the present invention, irrespective of the degree of operation on the accelerator pedal, driving force and braking force are controlled in a manner as described with reference to FIGS. 3(*a*) and (*b*).

FIGS. 8(*a*) and (*b*) respectively correspond to FIGS. 3(*a*) and (*b*). Dotted lines 401 and 403 are added, which respectively represent transition of operation angle of the acceleration pedal (more adequately, driving force produced responsive to the operation angle of the acceleration pedal in regular movement of the vehicle).

In FIG. 8(*a*), during time t2, as dotted line 401 indicates, the acceleration pedal is pressed a little and the operation angle increases, thereafter the acceleration pedal is released. Despite such operation of the acceleration pedal, in the start control during time t1-t3, the driving force is increased to the target driving force (dotted line 111) that is calculated to balance with the inclination, and the driving force is held at the target driving force till braking force is released to zero.

In FIG. 8(*b*), from time t1 to t3, as dotted line 403 indicates, operation angle of the acceleration pedal continue to increase responsive to pressing of the acceleration pedal. Despite such operation of the acceleration pedal, in the start control in time t1-t3, the driving force is increased to the target driving force (dotted line 111) that is calculated to balance with the inclination, and the driving force is held at the target driving force till braking force is released to zero.

Thus, while start control is being performed during time t1-t3, even if the acceleration pedal is pressed, start control unit 13 and driving force control unit 23 are configure not to respond to operation of the acceleration pedal. After time t3 when the start control is completed, movement control unit 15 controls driving force control unit so that driving force is produced responsive to the operation angle of the acceleration pedal. In FIG. 8(*a*), acceleration pedal is not pressed after time t3. Accordingly, movement control unit 15 increases the driving force toward a predetermined vehicle speed (for example, for the above mentioned following control, vehicle speed is controlled to follow the preceding vehicle). In FIG. 8(*b*), after time t3, the target driving force is the driving force corresponding to an increased operation angle of the acceleration pedal, and the driving force is produced in accordance with the target driving force.

Specific embodiments of the present invention have been described above. It should be noted that the present invention is not limited to these embodiments.

DESCRIPTION OF REFERENCE NUMBERS

10 movement control apparatus
11 stop and hold control unit
13 start control unit 17 inclination acquisition unit
21 braking force control unit
23 driving force control unit

The invention claimed is:

1. A movement control apparatus, comprising:
 a braking force control unit for controlling a braking force of a vehicle;
 a stop and hold control unit for holding the vehicle in a stop state via the braking force control unit;
 a driving force control unit for controlling a driving force of the vehicle;
 a start operation detector for detecting a start operation by a user;
 an acquisition unit for acquiring inclination of a road along which the vehicle moves;
 a start control unit that is configured to, when the start operation detector detects a start operation while the vehicle is held in the stop state by the stop and hold control unit:
  determine, based on the acquired inclination, a target driving force for suppressing movement of the vehicle on the road so that the target driving force is balanced with a force downward along the road,
  after the driving force control unit applies the target driving force to the vehicle, release the braking force via the braking force control unit to release holding the vehicle in the stop state, and
  responsive to releasing the braking force, increase the driving force via the driving force control unit to start the vehicle,
 wherein the start control unit maintains the vehicle, until the releasing of the braking force is completed, in a state where the vehicle is driven with the target driving force via the driving force control unit.

2. An apparatus of claim 1, wherein said target driving force is determined according to the magnitude of the inclination so that the vehicle does not move as the braking force is released.

3. An apparatus of claim 1, wherein when the direction of movement of the vehicle is climbing in the direction of the inclination, the start control unit controls start of the vehicle.

4. An apparatus of claim 1, wherein said target driving force is the driving force that can maintain the vehicle speed at zero even if the braking force is released, and wherein irrespective of the user's operation on an acceleration pedal, the vehicle is driven by the target driving force via the driving force control unit until the braking force is released via the braking force control unit.

5. An apparatus of claim 1, wherein the start control unit is configured to release the braking force by reducing said braking force gradually over a predetermined length of time via the braking force control unit to release holding the vehicle in the stop state, after the driving force control unit applies the target driving force to the vehicle, when the start operation detector detects a start operation while the vehicle is held in the stop state by the stop and hold control unit.

6. A method of claim 1, wherein the releasing of the braking force is performed by reducing said braking force gradually over a predetermined length of time.

7. A method for controlling movement of a vehicle, comprising:
 holding the vehicle in a stop state via control of a braking force;
 detecting a start operation of the vehicle by a user;
 acquiring inclination of a road along which the vehicle moves;
 controlling start of the vehicle when the start operation is detected while the vehicle is held in the stop state, said controlling comprises:
  determining, based on the acquired inclination, a target driving force that suppresses movement of the vehicle on the road so that the target driving force is balanced with a force downward along the road,
  applying the target driving force to the vehicle, and releasing the braking force to release holding the vehicle in the stop state,
  maintaining the vehicle until the releasing of the braking force is completed, in a state where the vehicle is driven with the target driving force, and
  responsive to releasing of the braking force, increasing the driving force to start the vehicle.

8. A method of claim 7, wherein said target driving force is the driving force that can maintain the vehicle speed at zero even if the braking force is released, and wherein said target driving force is calculated according to the magnitude of the inclination so that the vehicle does not move by releasing of the braking force.

9. A method of claim 7, wherein when the moving direction of the vehicle is opposite the descending direction of the inclination, the step of controlling start of the vehicle is performed.

10. A method of claim 7, wherein said target driving force is the driving force that can maintain the vehicle speed at zero even if the braking force is released, and wherein irrespective of user's operation on an acceleration pedal, the vehicle is driven by the target driving force until the braking force is released.

* * * * *